United States Patent
Nahar

(10) Patent No.: US 7,629,016 B2
(45) Date of Patent: Dec. 8, 2009

(54) PROCESS FOR PHOTOCHEMICAL ACTIVATION OF POLYMER SURFACE AND IMMOBILIZATION OF BIOMOLECULES ONTO THE ACTIVATED SURFACE

(75) Inventor: Pradip Nahar, Delhi (IN)

(73) Assignee: Council of Industrial and Scientific Research, New Delhi (IN)

( * ) Notice: Subject to any disclaimer, the term of this patent is extended or adjusted under 35 U.S.C. 154(b) by 61 days.

(21) Appl. No.: 10/166,292

(22) Filed: Jun. 10, 2002

(65) Prior Publication Data
US 2003/0228410 A1 Dec. 11, 2003

(51) Int. Cl.
*G01N 1/31* (2006.01)

(52) U.S. Cl. .................. 427/2.13; 435/7.1; 436/501; 436/518; 436/528; 436/44; 436/166; 427/2.11; 427/2.12; 427/487; 427/512; 427/520; 427/557

(58) Field of Classification Search .......... 435/4, 435/7.1, 7.8, 7.92, 174–182, 288.3, 288.4; 436/518, 532, 501, 528, 44, 166; 427/157, 427/160, 541, 553, 581, 582, 487, 491, 493, 427/508, 520, 2.11–2.13, 512, 517, 521, 427/554, 557, 558, 595, 596, 412.4, 414, 427/417; 534/579; 8/451, 466; 430/194–197

See application file for complete search history.

(56) References Cited

U.S. PATENT DOCUMENTS

| | | | | |
|---|---|---|---|---|
| 4,007,089 A | * | 2/1977 | Smith, III | 435/181 |
| 4,268,600 A | * | 5/1981 | Robillard et al. | 430/142 |
| 4,597,999 A | * | 7/1986 | Lingwood | 427/520 |
| 4,619,897 A | * | 10/1986 | Hato et al. | 435/182 |
| 4,664,978 A | * | 5/1987 | Wu et al. | 428/409 |
| 4,885,250 A | * | 12/1989 | Eveleigh et al. | 435/181 |
| 4,973,493 A | * | 11/1990 | Guire | 427/2.24 |
| 4,979,959 A | * | 12/1990 | Guire | 435/176 |
| 5,051,312 A | * | 9/1991 | Allmer | 428/458 |
| 5,079,155 A | * | 1/1992 | Cox et al. | 435/181 |
| 5,128,170 A | * | 7/1992 | Matsuda et al. | 427/2.24 |
| 5,158,880 A | * | 10/1992 | Eveleigh | 435/181 |
| 5,258,041 A | * | 11/1993 | Guire et al. | 435/181 |
| 5,270,193 A | * | 12/1993 | Eveleigh | 435/181 |
| 5,342,772 A | * | 8/1994 | Arenzen et al. | 530/413 |
| 5,554,501 A | * | 9/1996 | Coassin et al. | 506/9 |
| 5,741,551 A | * | 4/1998 | Guire et al. | 427/407.1 |
| 5,773,587 A | * | 6/1998 | Lowe et al. | 530/413 |
| 6,033,784 A | * | 3/2000 | Jacobsen et al. | 428/411.1 |
| 6,368,587 B1 | * | 4/2002 | Anders et al. | 424/78.18 |
| 6,498,016 B1 | * | 12/2002 | Nahar et al. | 435/7.92 |
| 6,669,994 B2 | * | 12/2003 | Swan et al. | 427/517 |
| 7,087,658 B2 | * | 8/2006 | Swan et al. | 522/36 |
| 2003/0036604 A1 | * | 2/2003 | Meisenburg et al. | 525/123 |

FOREIGN PATENT DOCUMENTS

GB 1377747 * 12/1974

OTHER PUBLICATIONS

Guire, P. Photochemical Immobilization of Enzymes and Other Biochemicals. Methods Enzymol. 1976;44:280-288.*
Nahar, P. et al. Light-Induced Activation of an Inert Surface for Covalent Immobilization of a Protein Ligand. Anal. Biochem. 2001;294:148-153.*
Forstinger, K. & Metz, H.J. Diazo compounds and diazo reactions. Ullmann's Encyclopedia of Industrial Chemistry, John Wiley & Sons, Inc., pp. 1-21 (online posting date Jun. 15, 2001).*
Koleske, J.V. Dual-Cure Mechanisms, in Radiation Curing of Coatings, Chapter 9, pp. 155-164, ASTM Int'l. (2002).*
Dole, M. Fluoropolymers, in The Radiation Chemistry of Macromolecules, Chapter 9, pp. 167-177, Malcolm Dole, Ed., Acad. Press, Inc. (1973).*
Moriarty, R.M. & Serridge, P. Thermal decomposition of geminal diazides. J. Am. Chem. Soc. 1971;93:1534-1535.*
Chapiro, A. Graft copolymers of polytetrafluoroethylene, in Radiation Chemistry of Polymeric Systems, Chapter XII, pp. 676-680, 688-691, John Wiley & Sons, Inc. (1962).*
Christe, K.O. et al. Syntheses, properties, and structures of anhydrous tetramethylammonium fluoride and its 1:1 adduct with trans-3-amino-2-butenenitrile. J. Am. Chem. Soc. 1990;112:7619-7625.*
Lal, G.S. et al. Electrophilic NF fluorinating agents. Chem. Rev. 1996;96:1737-1755.*

* cited by examiner

*Primary Examiner*—Gailene R Gabel
(74) *Attorney, Agent, or Firm*—John P. White; Cooper & Dunham LLP

(57) ABSTRACT

The invention relates to a photochemical process for the preparation of an activated polymer surface having an active fluoro group using 1-fluoro-2-nitro-4-azidobenzene to form the activated polymer surface and then immobilizing a biomolecule thereon by forming a covalent bond between the activated polymer surface and the biomolecule.

8 Claims, 6 Drawing Sheets

Figure 1:
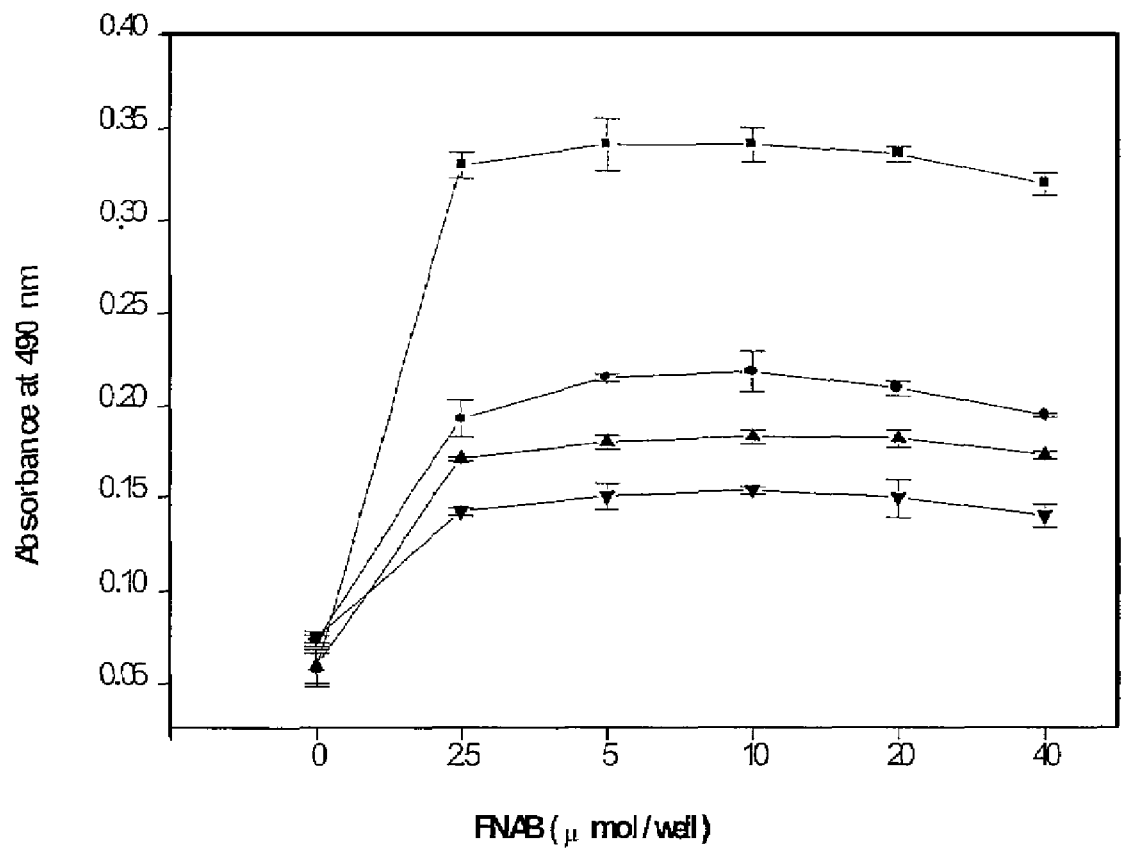

PROCESS FOR PHOTOCHEMICAL ACTIVATION OF POLYMER SURFACE AND IMMOBILIZATION OF BIOMOLECULES ONTO THE ACTIVATED SURFACE

FIELD OF THE INVENTION

The invention relates to a rapid and simple process for activation of inert polymer surface for immobilization of biomolecule. The activated surface can be used in clinical diagnostics, molecular biology, agriculture, environmental science, chemical or biochemical industry and many other related fields.

Immobilization of biomolecules onto natural or synthetic polymer is of particular interest because of their application in clinical laboratories, biosensors, membrane bioreactors, diagnostics and many other relevant fields. As most of these polymers are inert, they require special treatment for activation. Introduction of various functional groups onto the inert surface by chemical reaction (s) has gained popularity in recent years as the activated surface thus prepared can immobilize biomolecule by stable chemical bonding.

BACKGROUND AND PRIOR ART

Immobilization of enzymes to synthetic polymer is of particular interest because of their application in clinical laboratories, biosensors, membrane bioreactors and diagnostics [Krysteva, M. A., Shopova, B. L., Yotova, I. Y., and Karasavova, M. I. (1991) Biotechnol Appl Btochem. 13, 106-111; Pandey, P. C., Kayastha, A. M., and Pandey, V. (1992). Appl. Biochem. Biotechnol. 33, 139-144]. There are different methods for immobilization of biomolecules on to a polymer surface e.g. entrapment, encapsulation, adsorption, covalent binding etc. Covalent immobilization is often necessary for binding molecules that do not adsorb, adsorb very weakly, or adsorb with improper orientation and conformation to polymer surfaces. This may result in better biomolecule activity, reduced nonspecific adsorption, and greater stability [Bangs, L. B., and Meza, M. B. (1995) Microspheres, part 2: Ligand attachment and test formulation. MD & DI's IVD Technol. 20-26; Larsson, P. H., Johansson, S. G. O., Hult, A., and Gothe, S. (1987) J Immunol Meth. 98, 129-135; Rasmussen, S.R., Larsen, M. R., and Rasmussen, S. E. (1991) Anal Biochem. 198, 138-142; Chevrier, D. Rasmussen, S. R., and Guesdon, J. L. (1993) Molec Cell Probes. 7, 187-197]. There are a number of ways to modify solid supports for the covalent immobilization of biomolecules. Aleixo et al. (1985) introduced an active functional group to an inert polystyrene surface by nitrating the aromatic ring of the polystyrene followed by the reduction of the nitro group to amino group; the amino polystyrene was further activated by a chemical reaction such as diazotization for covalent immobilization of protein.

Immobilization of biomolecules onto an inert polypropylene (PP) or polyethylene (PE) surface is of special interest because of their inability to bind through adsorption (unlike polystyrene) and their insolubility in most of the organic solvents. However, immobilization of biomolecules onto PP and PE surfaces is restricted due to the absence of any active functional group on them for chemical bonding. Therefore, it is necessary to activate these surfaces for immobilization of biomolecules. Activation of PP and PE surfaces has been reported to occur through radiation graft polymerization or gaseous plasma technique [de Queiroz et al., (1997) J. Biomater. Sci. Polym. 8, 667-681; Kaetsu, I. et al. (1980) J. Biomed. Mater. Res. 14, 199-210; Sipehia, R. et al. (1988) J Biomed. Mater. Res. 22, 417-422; Sipehia, R. (1998-99) Biomater. Artif. Cells Artif. Organ 16, 955-966.; Hayat, U. et al. (1992) Biomaterials 13, 801-806 and Wang, C. C. et al. (1993) J. Biomater. Sci. Polym. 4, 357-367]. For example, functional groups were introduced on the PE surface by copolymerization of ethylene with acrylic acid or acrylamide using gamma rays from a $^{60}Co$ source for immobilization of albumin [de Queiroz et al., (1997) J. Biomater. Sci. Polym. 8, 667-681; Wang, C. C. et al. (1993) J. Biomater. Sci. Polym. 4, 357-367 and Sano, S. et al. ?( ) 20 993) Biomaterials 14, 817-822]. PP and PE surfaces can also be activated by introducing hydroxyl or amino groups by a plasma technique employing oxygen [Sipehia, R. (1998-99) Biomater. Artif. Cells Artif. Organ 16, 955-966] anhydrous ammonia [Sipehia, R. et al. (1988) J Biomed. Mater. Res. 22, 417-422; Hayat, U. et al. (1992) Biomaterials 13, 801-806] or decylamine hydrochloride [Terlingen, J. G. et al. (1993) J. Biomater. Sci. Polym. 4, 165-181]. The immobilization of enzymes such as glucose oxidase, peroxidase, and protein A and antibody on surfaces having an amino group has been achieved through a glutaraldehyde coupling method [Sipehia, R. et al. (1988) J Biomed. Mater. Res. 22, 417-422; Hayat, U. et al. (1992) Biomaterials 13, 801-806].

Guire had activated aminoalkyl matrix thermochemically with 1-fluoro-2-nitro-4-azidobenzene (FNAB) in 16-64 hours followed by attachment of the enzyme through the photochemical reaction in 2-16 hours [Patric, G. (1976) Method. Enzymol. 44, 280-288; U.S. Pat. No. 3,959,078]. Similarly, U.S. Pat. No. 4,973,493 describes a method where hydroxyl-bearing support was activated thermochemically with 1-fluoro-2-nitro-4-azidobenzene. Major drawbacks of the above procedures are that both the steps (activation and immobilization) are time consuming and cumbersome. Moreover, method of Guire gives the limiting choice of the matrix i.e. matrix must have an amino or similar nucleophillic group. Other major drawbacks are that the reactive nitrene, formed under UV exposure binds randomly with almost all the ingredients present there including biomolecule, matrix or solvent resulting in undesirable reactions which may lead to inefficient immobilization.

The photochemical method permits the covalent attachment of active functional group onto inert solid surface under gentle reaction conditions [Amos, R. A. Anderson, A. B., and Clapper, D. L. (1995) In Encyclopedic Handbook of Biomaterials and Bioengineering. Part A: New York, Marcel Dekker, 895-926]. This method is normally based on a compound having at least two functional groups of which one is essentially a photoactivable group. There are different methods for activation of inert surfaces through a photolinker. But in most of the methods, either the photoactivable compound is expensive or difficult to prepare or the procedure is cumbersome and time consuming.

In U.S. Pat. No. 4,973,493 describe the method for the modification of a polymer surface by attaching biocompatible agents like growth factor, fibronectin, collagen etc by using N-oxy succinimide esters of 4-azido-2-nitrophenyl epsilon amino caproic acid, 4-azido-2-nitrophenyl amino undecanoic acid and benzoylbenzoic acid. However, these modified surfaces are used for specific purpose like cell attachment.

U.S. Pat. No. 5,427,779 describes a method for the modification of an inert surface by a two-ring heterocyclic photolinker such as psoralenes in a photochemical reaction (2 hour irradiation at 350 nm). Biotinylated psoralenes were also used.

Disadvantages of these methods are i) posralenes are difficult to synthesize, ii) expensive, iii) require long irradiation time for bonding with the support and iv) during activation with biotinylated psoralenes, activated polymer is not generally applicable.

U.S. Pat. No. 6,033,784 and PCT no. WO 96/31557 discloses a method for photochemical modification using quinones. Using primary amino containing quinone derivative amino group was introduced onto polystyrene surface by UV irradiation followed by washing and drying for 50 minutes at 60° C. Similarly, acid group was introduced onto the polystyrene surface. These groups can not easily bind with the protein without addition of one or more activating reagent. More over preparation of such plates and photolinker are time consuming and cumbersome. These activated surfaces were also not suitable for protein binding or ELISA.

None of the above methods gives an activated surface, which is stable in light and capable of forming a covalent bond with the biomolecule more preferably, protein molecule. Since all of these methods are tedious and time consuming, there is a need for a convenient and direct technique allowing introduction of active functional groups onto inert surfaces which immobilize biomolecule by directly reacting with the nucleophilic group of the biomolecule.

OBJECTS OF THE INVENTION

The main object of the present invention is to prepare activated polymer surface capable of forming a covalent bond with the biomolecule under mild conditions.

Another object of the present invention is to make the method mild, simple and quick.

Yet another object of the present invention is to make activated polymer surface by photochemical reaction of 1-fluoro-2-nitro-4-azidobenzene with the polymer surface.

Yet another object of the present invention is to make activated polymer surface for rapid and efficient immobilization of biomolecule.

Yet another object of the present invention is to make activated polymer surface useful for immobilization of biomolecule required for chemical industry, pharmaceutical industry, food industry as well as for diagnostic purpose.

Yet another object of the present invention is to find a cheap and non-hazardous source of energy for carrying out photochemical reaction.

Yet another object of the present invention is to find a method for large-scale activation of polymer surface.

SUMMARY OF THE INVENTION

With a view to achieve the objective of the present invention and overcoming the disadvantage of the known method for the activation of polymer surface, a rapid, simple and efficient method is disclosed for activation of inert polymer which can be used directly for immobilization of biomolecule.

Accordingly, the present invention provides a process for the preparation of activated polymer surface capable of forming a covalent bond with the biomolecule which comprises coating the surface of a polymer by a photolinker more particularly by 1-fluoro-2-nitro-4-azidobenzene and subjecting the dry photolinker-coated polymer surface to light irradiation preferably by UV light or sunlight for a period ranging from 1 second to 60 minutes followed by removing the unattached compound by washing thoroughly with a organic solvent preferably methanol and drying at an ambient temperature.

One feature of the present invention is that the activated surface can be used for immobilization of molecules having a nucleophilic group such as amino group.

Another feature of the present invention is that the activated surface has a potential for versatile applications such as in diagnostics for carrying out enzyme-linked immunosorbent assay, in biosensor, in proteomics, in combinatorial chemistry, in organic reactions involving enzyme and many other fields where immobilized molecule is required.

Another feature of the present invention is that photolinker used is commercially available or can be made easily.

Another feature of the present invention is that photolinker is coated onto the polymer surface using an organic solvent. Another feature of the present invention is that dry photolinker-coated polymer surface is exposed to UV light.

Another feature of the present invention is that the organic solvent is evaporated completely from the photolinker-coated surface before exposure to light.

Another feature of the present invention is that activation of the polymer surface can also be carried out by exposing polymer and photolinker in presence of a non-hydrogen containing solvent like carbontetrachloride.

Another feature of the present invention is that sunlight can be used for activation of the polymer.

Another feature of the present invention is that activation of polymer surface can be carried out in a large scale.

Another feature of the present invention is that almost all the organic polymer can be activated by the invented method. Minimum prerequisite of the polymer is that it should contain carbon-hydrogen bonds, which are available in almost all the polymers.

BRIEF DESCRIPTION OF ACCOMPANYING DRAWINGS

FIG. 1. Time and dose-dependent activation of polystyrene microtiter wells. 2.5-40 μmol FNAB per well was taken and exposed to UV irradiation for 5 min (▼), 10 min (▲), 20 min (●) and 40 mim (■). Control experiments were carried out with untreated wells (FNAB: 0 μmol) HRP was immobilized on the activated and control wells and its subsequent reactions with the substrate were assayed colorimetrically (Example 1).

Figure 2:
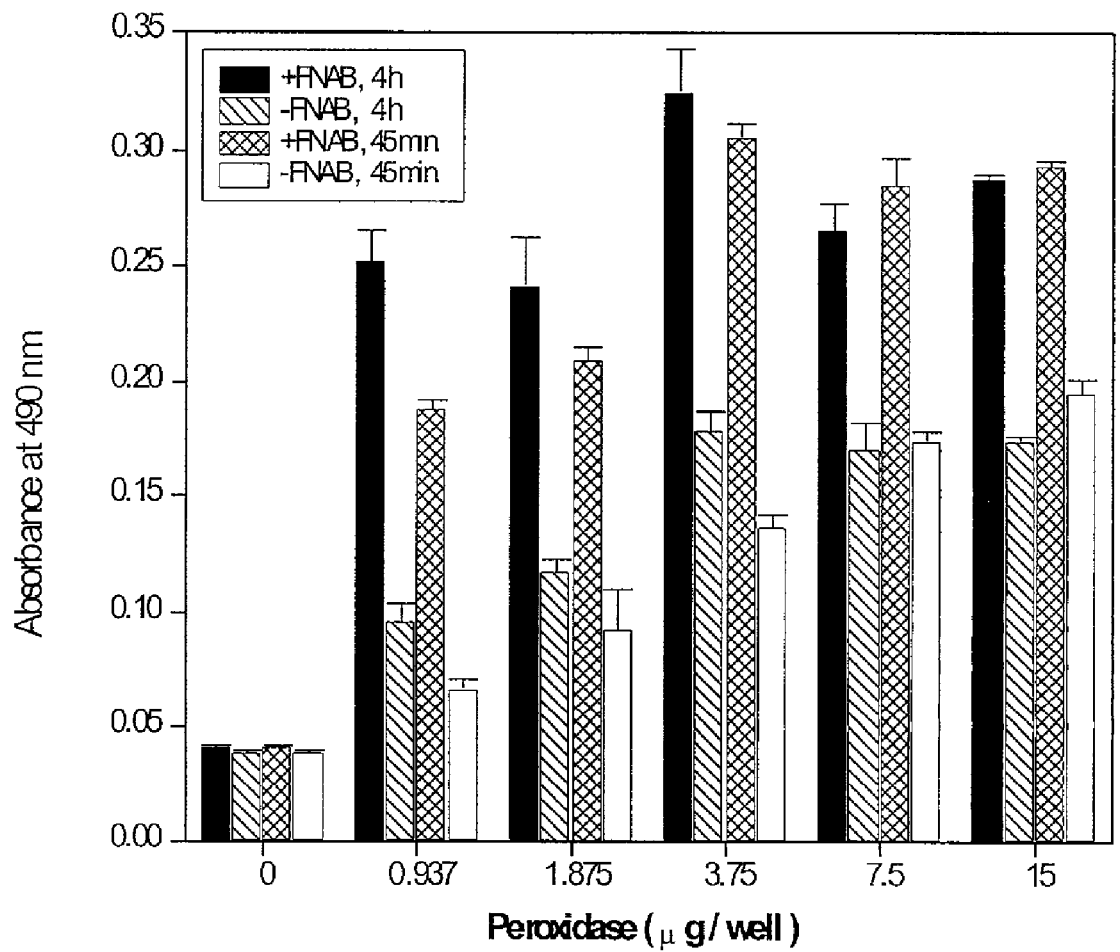

FIG. 2. Time and dose-dependency for immobilization of HRP at 37° C. on the wells of treated (+FNAB) and untreated (−FNAB) polystyrene microtiter plates. Optimum amount of HRP required for immobilization is determined by taking 0-15 μg HRP per well in the FNAB treated wells followed by incubation at 37° C. for 45 min and 4 h. Parallel control experiments were carried out with the untreated wells. Immobilized HRP was assayed colorimetrically after adding substrate as in the text (Example 2).

Figure 3:
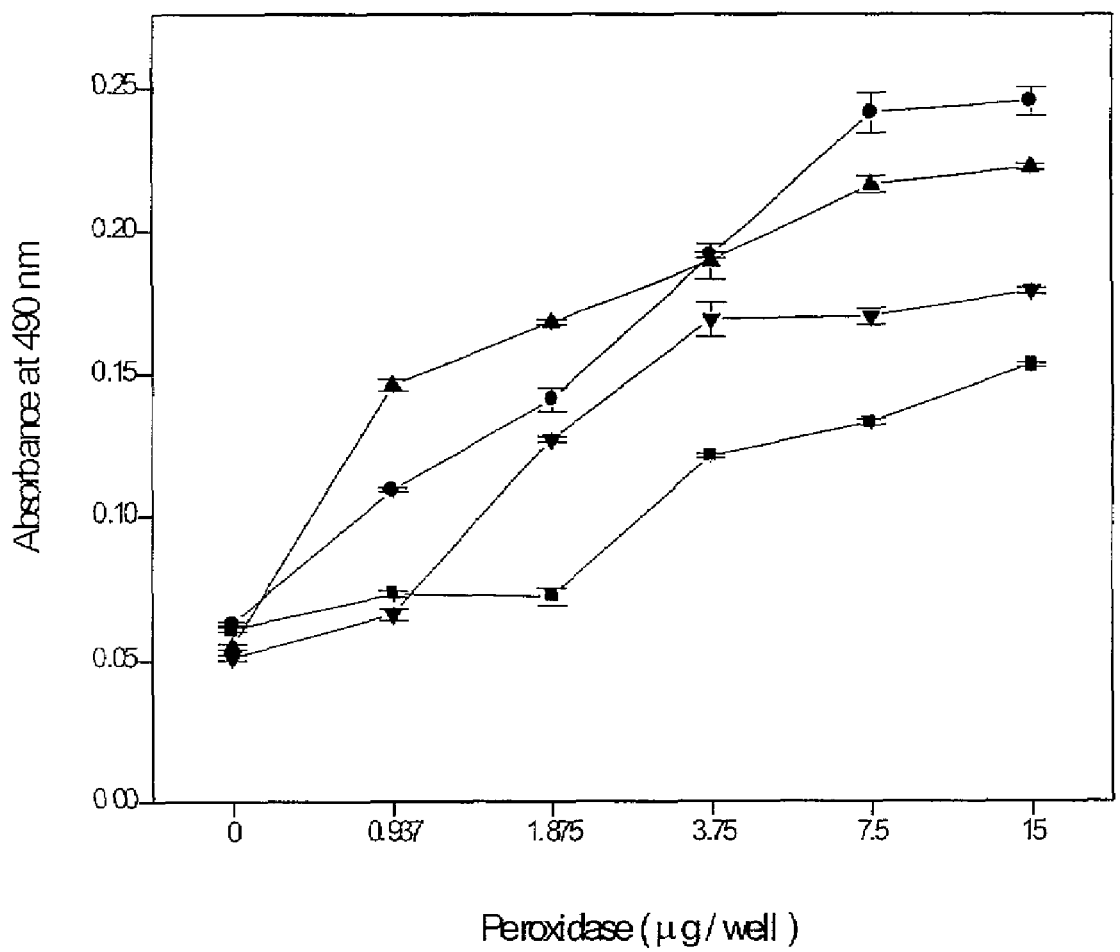

FIG. 3. Effect of FNAB activation on binding capacity of microtiter wells. 0-15 μg of HRP per well was taken for immobilization on FNAB treated low binding polystyrene microwells (Tarson, Kolkata, India) and high binding polystyrene NUNC-MAXISORP™ microwells (eBioscience, Inc., San Diego, Calif.). Experiment for immobilization of HRP on untreated wells of both the plates was taken as control. Absorbance recorded after adding substrate-dye buffer to the HRP immobilized wells and represent activated low binding and high binding polystyrene microwells, respectively, whereas ▼ and ■ represent untreated low binding and high binding polystyrene wells, respectively (Example 3).

Figure 4:
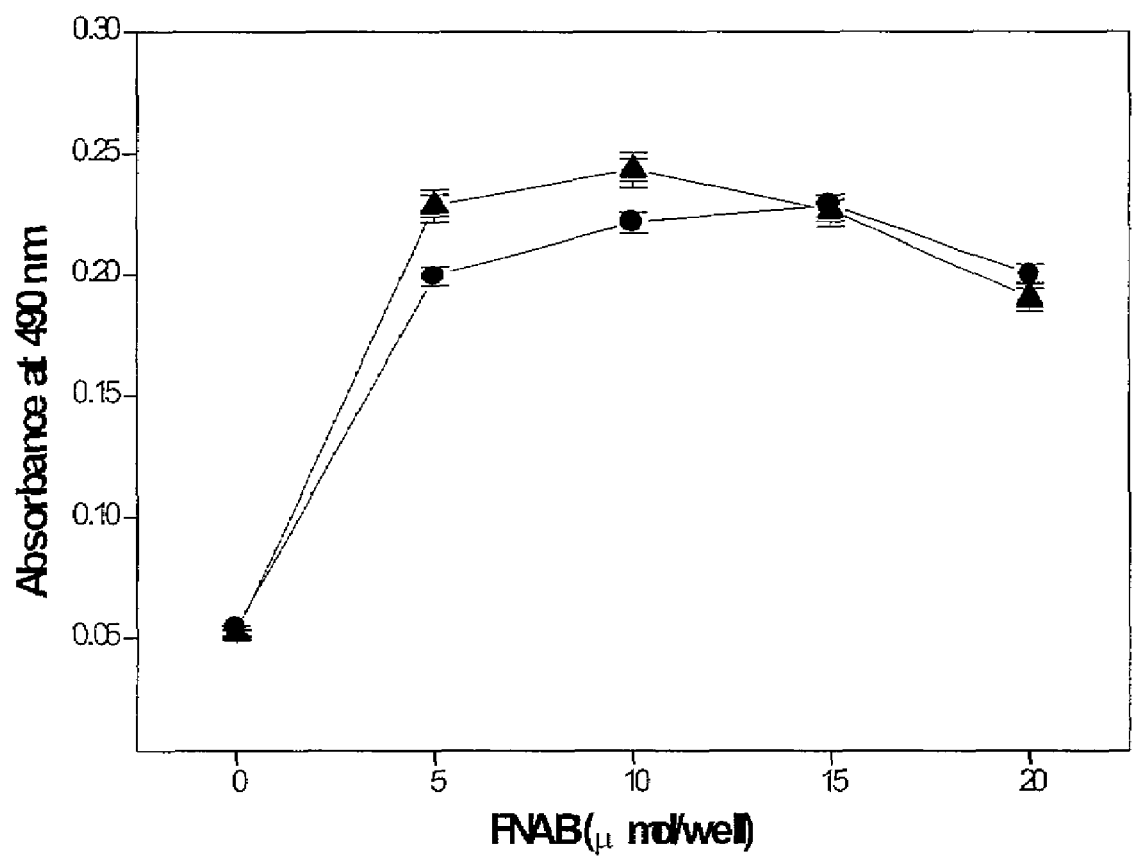

FIG. 4 Dose dependent activation of polystyrene microtiter wells. The amount of 5-20 μmol FNAB per well was taken and exposed to sunlight (▲) for 20 min. Simultaneous experiment was carried out in UV stratalinker® (Stratagene Corp., California, USA) (●) for the activation of the plate. Control experiment was carried out with untreated wells (FNAB: 0 μmol). HRP was immobilized on the activated and control wells, and its subsequent reactions with the substrate were assayed colorimetrically (Example 4).

Figure 5:
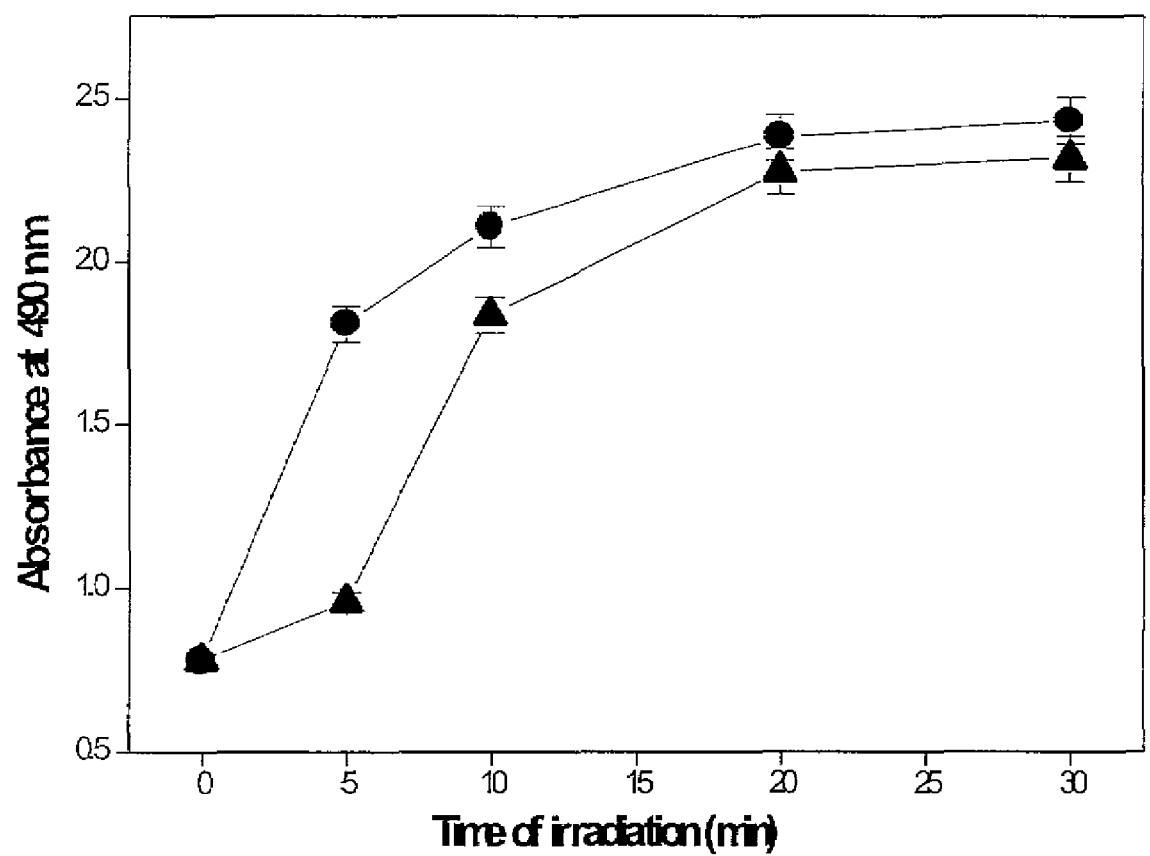

Fig. 5 Comparative study of the mode of activation of polystyrene plate. 10 μmol FNAB per well was exposed to U.V irradiation (▲) and simultaneous experiment is run under sunlight (●) for 5, 10, 20 and 30 min. Control experiment were carried out with untreated wells (FNAB: 0 μmol). HRP was immobilized on the activated and control wells and its subsequent reactions with the substrate were assayed colorimetrically (Example 5).

Figure 6:
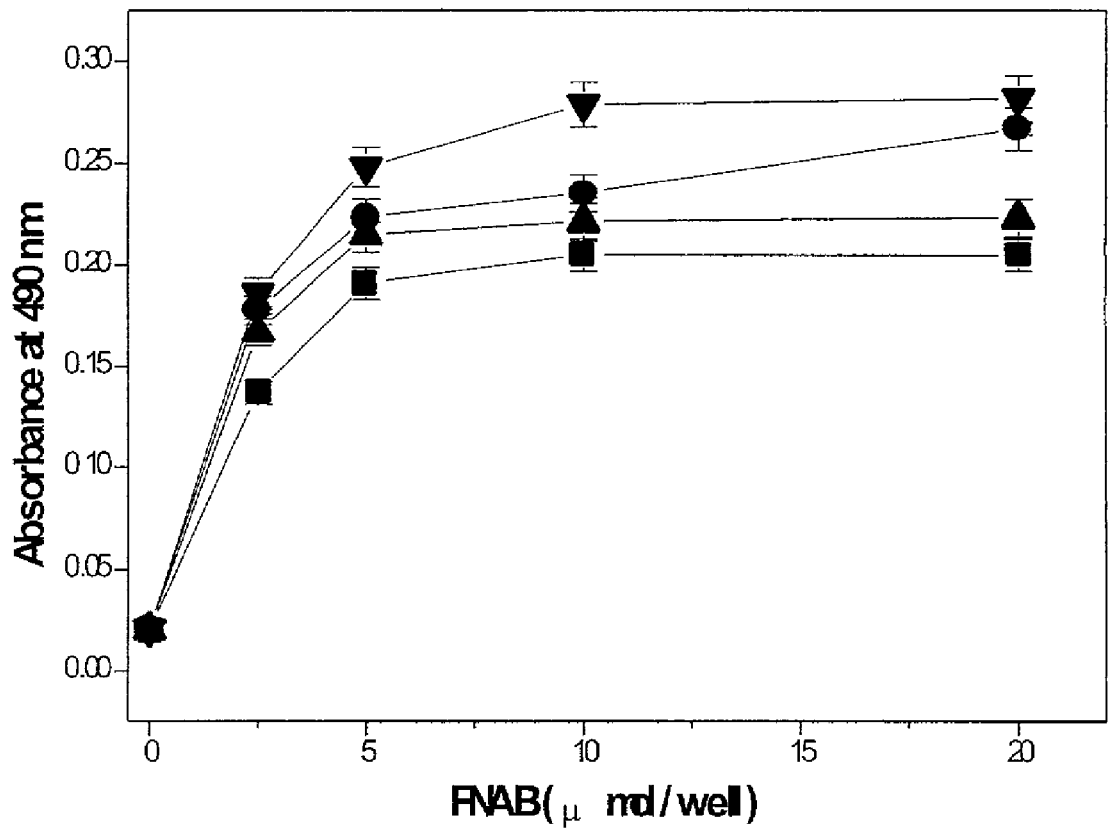

FIG. 6 Activation of PP microtiter wells as a function of FNAB concentration and UV exposure. FNAB (2.5-20 μmol) per well was taken and exposed to U.V light (365 nm) for 5 min (■), 10 min (●), 20 min (●)and 40 min (▼). Control experiments were carried out with untreated wells (FNAB: 0 μmol). Horseradish peroxidase was immobilized onto the activated and control wells, and its subsequent reactions with the substrate were assayed colorimetrically (Example 6).

DETAILED DESCRIPTION OF THE INVENTION

Accordingly, the present invention provides a rapid, simple and efficient process for the preparation of an activated polymer surface from an inert polymer having carbon-hydrogen bonds for immobilization of biomolecule, the said process comprising steps of:
(a) coating the inert polymer surface with the photolinker dissolved in a suitable organic solvent,
(b) evaporating the organic solvent of step (a) from the coated surface at room temperature in dark,
(c) subjecting the surface of photolinker coated polymer of step (b) to photo irradiation for a period ranging from 1 second to 60 minutes,
(d) washing the irradiated surface of step (c) with a suitable organic solvent,
(e) drying the washed surface of step (d) at an ambient temperature and
(f) using activated polymer surface of step (e) for immobilization of biomolecule for diagnostic, drug screening, proteomics, combinatorial and other applications.

One embodiment of the present invention provides a process in which the polymer surface used for activation is selected from polystyrene, polyethylene, polypropylene, polycarbonate, polyvinyl alcohol, polyvinyl chloride and polymers having carbon-hydrogen bond.

Another embodiment of the invention relates to shape of polymer surface which is selected from stick, microtiter plate, sheet, tube, well, cuvet and the like.

Still another embodiment of the invention provides a process in which photolinker compound used is 1-fluoro-2-nitro-4-azidobenzene.

Still another embodiment, the source of photoirradiation is selected from UV light, sunlight, flash light, laser beam and preferably sunlight.

In yet another embodiment, the photoirradiation is carried out for a period in the range of 1 seconds to 60 minutes and preferably 40 minutes yet another embodiment, the photoreaction between the polymer surface and the photolinker compound is carried out in dry condition or in non-hydrogen containing solvent is carbon-tetrachloride.

Still yet another embodiment, the activated surface is used for covalent immobilization of biomolecule is selected from enzyme, antigen, antibody and peptide.

Yet another embodiment, the activated surface can potentially be used in ELISA and other clinical diagnostics, molecular biology, proteomics, genomics, agriculture, environmental science, chemical or biochemical industry and many other related fields.

Yet another embodiment, the time required for immobilization of biomolecule is in the range of 30 minutes to 5 hours and preferably 45 minutes. Yet another embodiment of the present invention provides a process wherein the temperature range to bring about immobilization of biomolecule is in the range 0° C. to 50° C. A process as claimed in claim 1 is commercially exploited Yet another embodiment of the invention provides a non-hazardous and eco friendly process.

The present comprises a rapid and efficient method for activation of inert polymer using a photolinker, 1-fluoro-2-nitro-4-azidobenzene. 1-fluoro-2-nitro-4-azidobenzene upon irradiation under UV light generates highly reactive nitrene, which binds to the inert surface whereas fluorine atom of the photolinker reacts thermochemically with the amino group of protein.

Yet another embodiment, use of solvent such as carbontetrachloride during activation found to have advantage especially for uniform activation of tube-shaped surface.

Yet another embodiment, the photoirradiation is performed under anhydrous or solvent free condition.

In yet another embodiment, comparison if immobilization of HRP on treated and untreated surfaces of low binding and high binding polystyrene microtiter plates were studied.

In yet another embodiment, the photochemical activation of inert surface like polystyrene, polyethylene, polyvinyl chloride etc. can be carried out with FNAB through the formation of covalent bond. As the choice of matrix is quite large by our method, therefore it will be easy to find specific matrix for a specific use such as in bioreactor, biostrip, biosensor or even for simple assay development.

Yet another embodiment, immobilization of enzyme onto a polymer is very simple, rapid, and cheap and overcomes the drawbacks of the reported methods.

In an embodiment of the present invention, the photolinker is selected from a compound having at least one photochemical group, at least one active thermochemical group and may optionally have other functional group(s) not directly involved in the chemical reaction.

In an embodiment of the present invention photochemical group is selected from a group capable of forming a covalent bond with the polymer when exposed to light.

In an embodiment of the present invention active thermochemical group is selected From a group which is not photo sensitive and capable of forming a covalent bond with the nucleoplilic group of the molecule without addition of any other catalyst or reagent.

In an embodiment of the present invention other functional group is selected from a group which is not directly involve in the photochemical or thermochemical reaction but accelerate either or both the reactions to proceed in the desired direction.

In an embodiment of the present invention photochemical group used is azido group.

In an embodiment of the present invention active thermochemical group used is fluoro group.

In an embodiment of the present invention other functional group used is nitro group.

In yet another preferred embodiment of the present invention, photolinker is selected from 1-fluoro-2-nitro-4-azidobenzene.

In yet another embodiment of the present invention polymer is selected from any polymer having carbon-hydrogen bonds.

In yet another preferred embodiment of the present invention polymer is selected from carbon-hydrogen containing organic polymer, inorganic polymer, natural polymer etc.

In yet another preferred embodiment of the present invention polymer is selected from polystyrene, polyethylene, polypropylene, polycarbonate, polyvinyl chloride, polyvinyl alcohol, carbon-hydrogen containing glass, controlled pore glass, silica and alike.

In yet another embodiment of the present invention photolinker is dissolved in a suitable solvent for coating the polymer surface uniformly.

In yet another embodiment of the present invention, suitable solvent is selected from a group of solvents having a property of dissolving the photolinker but not the polymer and preferably its boiling point should be less than 100° C.

In yet another preferred embodiment of the present invention, suitable solvent is selected from methanol, ethanol, carbon tetrachloride and alike.

In yet another preferred embodiment of the present invention, solvent is removed before exposure to light from the photolinker-coated polymer, in case a hydrogen containing solvent is used.

In yet another preferred embodiment of the present invention, hydrogen-containing solvent is selected from ethyl alcohol, methyl alcohol and alike.

In yet another preferred embodiment of the present invention solvent is not removed before exposure to light from the photolinker-coated polymer, in case a non-hydrogen containing solvent is used.

In yet another preferred embodiment of the present invention, nonhydrogen-containing solvent can be used is carbon tetrachloride.

In yet another preferred embodiment of the present invention, photolinker-coated polymer surface is photoirradiated by UV light, sunlight, laser beam and alike for a period ranging from 1 second to 60 minutes.

In yet another preferred embodiment of the present invention, photolinker-coated polymer surface is photoirradiated by non-ionizing electromagnetic radiation in the wavelength ranging from UV to visible light for a period less than 60 minutes.

In yet another preferred embodiment of the present invention, photolinker-coated polymer surface is photoirradiated by sunlight for a period less than 60 minutes.

In yet another preferred embodiment of the present invention, photoirradiated surface is washed by a solvent having a property of dissolving the photolinker and its degraded products and also not dissolving or distorting the polymer.

In yet another preferred embodiment of the present invention, shape of the polymer surface is selected from microtiter plate, well, sheet, tube, stick, cuvet and alike.

In further embodiment of the present invention, activated surface is used for immobilization of molecule selected from organic molecule or biomolecule having a nucleophilic group.

In further embodiment of the present invention, activated surface is used for immobilization of biomolecule selected from protein, nucleic acids, carbohydrate, oligonucleotides and alike.

In further embodiment of the present invention, activated surface is used for immobilization of protein selected from pharmaceutical important protein, industrial important protein, enzyme, antigen, antibody and alike.

In further embodiment of the present invention, activated surface can potentially be used in ELISA, clinical diagnostics, molecular biology, proteomics, genomics, agriculture, environmental science, chemical or biochemical industry and many other related fields.

Concentration of the photolinker as well the time of its exposure to UV light was very important for obtaining optimum activation of a polymer surface. Applied photolinker concentration at which optimum activation was observed was found to be 10 µM/well (FIG. 1), after which it decreased slightly or practically remained constant. Rearrangement of the nitrene moiety and reaction with the solvent is known to occur photochemically. To exclude the reaction of methanol with the highly reactive nitrene we have evaporated the solvent from the wells prior to exposure to UV light.

However, in presence of a non-hydrogen containing solvent like carbontetrachloride, results is found same as in case of dry photolinker coated surface.

The optimum time for exposure of the photolinker to UV light is found to be 20 minutes, though, at 40 minutes O.D. is quite high (FIG. 1). This was not desirable, as the whole well turned yellow by this time (40 min) due to degradation of photolinker that start adhering to the wells which is difficult to remove even after thorough washing.

For all our experimental work, the polystyrene surface was activated by using photolinker at a concentration of 10 µM/well with the UV exposure time of 20 minutes. Onto this activated surface different concentrations of HRP were immobilized at 4° C. for 4 h and 45 minutes respectively. Parallel experiment was performed at 37° C. also and control experiment was carried out with the untreated surface simultaneously.

The results showed that there is a significant increase in absorbance with respect to the linker treated wells as compared with untreated wells (FIG. 2). At 37° C. of enzyme immobilization (FIG. 2), there is a significant difference in absorbance between the enzyme immobilized via photolinker as compared with the directly immobilized one in a concentration range of (0.937 µg/well-3.75 µg/well). At 3.75 µg/well of enzyme, around three fold of difference in absorbance between the linker mediated immobilization and directly adsorbed enzyme was observed at both the temperatures. The best immobilization of enzyme onto the treated wells was observed at 37° C. in 45 minutes.

Hence, the activated surface is of great importance for immobilization of smaller amounts of proteinaceous ligands, which are precious or not affordable in large quantities. Immobilization onto the activated surface made in the present invention is very simple, fast and efficient.

The results showed that, in both the plates, the FNAB activation increases the efficiency of immobilization (FIG. 3). Moreover, the low binding polystyrene surface showed better immobilization after activation than the commercially available high binding Nunc maxisorp plates without activation.

It has also been invented that sunlight can be used for activation of inert polymer. Not much differences were obtained between sunlight mediated activation and UV light at 365 nm (in UV Stratalinker) mediated activation of inert polymer (FIG. 4 and FIG. 5). Hence, sunlight could be an excellent source for large-scale activation of polymer surface in presence of a photolinker.

The optimum amount of photolinker and the optimum time of its exposure to UV light were also determined for preparing activated PP microwells that allowed optimum activation. For activation of PP surface, the results displayed a pattern, which was akin to that of polystyrene surface. Maximum activation was obtained when 10 μmol FNAB per well was used at an optimum exposure time of 20 min, beyond which the surface discolored. On the other hand, control experiments (without FNAB) showed insignificant absorbance (FIG. 6). Efficient activation of the PE surface (1 cm$^2$) was also realized under the same conditions (FNAB, 10 μmol; irradiation time, 20 min). These conditions, therefore, appeared to provide a standard protocol for activation of different polymers with approximately the same surface area.

The light-induced activated surfaces thus prepared were found to be stable when kept at 37° C. and 4° C. under dry conditions for two months. At the end of this period, HRP was immobilized on these plates with the same efficacy as that with freshly prepared activated plates. This was evident from the fact that HRP immobilized on the 2-months old plates and freshly prepared activated plates showed absorbance values of 0.269 (when kept at 37° C.) and 0.278 (when kept at 4° C.) compared with a value of 0.282 (freshly-prepared plate) when assayed.

The photochemical activation of inert surface like polystyrene, polyethylene, polyvinyl chloride etc. can be carried out with FNAB through the formation of covalent bond. As the choice of matrix is quite large by our method, therefore it will be easy to find specific matrix for a specific use such as in bioreactor, biostrip, biosensor or even for simple assay development.

This method of immobilization of enzyme onto a polymer is very simple, rapid, and cheap and overcomes the drawbacks of the reported methods.

The process details of the present invention is as follows:

1-fluoro-2-nitro-4-azidobenzene (FNAB) is prepared from 4-fluoro-3-nitroaniline by diazotization reaction. The product was recrystallised from light petroleum (b.p. 40° C.-60° C.) to give straw colored needles, m.p. 52° C., which was stored in dark, at 4° C., moistened with water.

Substrate dye buffer is freshly prepared by mixing 99 ml of PBS (pH-7.2), 1 ml of 1:100 diluted $H_2O_2$ (30%W/V) and 0.6 ml of 1% o-dianisidine solution.

Washing Buffer is prepared by adding 0.05% Tween 20 to PBS (NaCl 0.85%, $Na_2PO_4$ 0.1M). 3 M NaOH is used as stop solution.

Photoirradiation was carried out at a wavelength of 365 nm in an UV Stratalinker; model-2400, (Stratagene, USA) fitted with five 15-watts tube light or under bright sunlight.

All the solutions were freshly prepared in triple distilled water before use. Absorbance values were expressed as the means±S.D for three determinations.

TABLE 1

Prior arts and their drawbacks

| Prior art | Drawbacks |
|---|---|
| 1. Inert polystyrene surface is activated by nitration, followed by reduction (Aleixo et al. 1985). Immobilization of protein onto the amino polystyrene was carried out through diazotization reactions. | Cumbersome, time-consuming multistep procedure. Activated polymer (amino polystyrene) needed further activation for protein immobilization. |
| 2. Activation of PP and PB surfaces has been achieved through radiation graft polymerization or gaseous plasma technique [de Queiroz et al., (1997); Kaetsu, I. et al. (1980); Sipehia, R. et al. (1988); Sipehia, R. (1998-99); Hayat, U. et al. (1992) and Wang, C. C. et al. (1993) | Cumbersome, time consuming multistep procedure. Activated polymer (amino, hydroxyl, or carboxyl bearing polymer) needed further activation for protein immobilization. |
| 3. Amino- or hydroxyl bearing matrix were activated thermochemically with 1-fluoro-2-nitro-4-azidobenzene (FNAB) in 16-64 hours followed by attachment of the enzyme through the photochemical reaction in 2-16 hours [Guire, (1976) Method. Enzymol. 44, 280-288; U.S. Pat. No. 3,959,078 and 4,973,493]. | Both the steps (activation and immobilization) are time consuming and cumbersome. Moreover, method gave limiting choice of the matrix i.e. matrix must have an amino-, hydroxyl or similar nucleophilic group. Other major drawbacks are that the reactive nitrene, formed under UV exposure binds randomly with almost all the ingredients present there including biomolecule, matrix or solvent resulting in undesirable reactions which may lead to inefficient immobilization. |
| 4. U.S. Pat. No. 5,427,779 describes a method for the modification of an inert surface by a two-ring heterocyclic photolinker such as psoralens in a photochemical reaction (2 hour irradiation at 350 nm). Biotinylated psoralens were also used. | i) psoralens are difficult to synthsize, ii) expensive, iii) require long irradiation time for bonding with the support and iv) during activation with biotinylated psoralens, activated polymer is not generally applicable. |
| 5. In U.S. Pat. No. 4,973,493 describe the method for the modification of a polymer surface by attaching biocompatible agents like growth factor, fibronectin, collagen etc by using N- oxy succinimide esters of 4-azido-2-nitrophenyl epsilon amino caproic acid, 4-azido-2-nitrophenyl amino undecanoic acid and benzoylbenzoic acid. | Cumbersome, time-consuming multi step procedure for the preparation of the photolinker. Activation also time-consuming method. These modified surfaces are used for specific purpose like cell attachment and not for general purpose. |
| 6. U.S. Pat. No. 6,033,784 and PCT no. WO 96/31557 discloses a method for photochemical modification using quinones. Using primary amino containing quinone derivative amino group was introduced onto polystyrene surface by UV irradiation followed by washing and drying for 50 minutes at 60° C.. Similarly, acid group was introduced onto the polystyrene surface. | These groups can not easily bind with the protein without addition of activating reagent. More over preparation of such plates and photolinker are time consuming and cumbersome. These activated surfaces were also not suitable for direct protein binding or carrying out ELISA. |

TABLE 2

The present invention and its advantages

| PRESENT INVENTION | ADVANTAGES |
|---|---|
| 1. The present invention provides a method for the preparation of activated polymer surface capable of forming a covalent bond with the biomolecule. The activated surface is prepared by a photolinker 1-fluoro-2-nitro-4-azidobenzene in a photochemical reaction by UV light or sunlight in 5-20 minutes, followed by treating the activated polymer with biomolecules to bring about immobilization of biomolecules. | 1. The activated surface can be used for immobilization of molecules having a nucleophilic group such as amino group. 2. The activated surface has a potential for versatile applications such as in diagnostics for carrying out enzyme-linked immunosorbent assay, in biosensor, in proteomics, in combinatorial chemistry, in organic reactions involving enzyme and many other fields where immobilized molecule is required. 3. Photolinker used is commercially available or can be made easily. 4. Light-induced activation of the polymer surface is carried out in dry condition. Hence, undesirable reaction with the solvent or polymer is eliminated in contrary to the prior |

TABLE 2-continued

The present invention and its advantages

| PRESENT INVENTION | ADVANTAGES |
|---|---|
| | arts where photochemical immobilization is carried out rather than activation.<br>5. Sunlight can be used for large-scale activation of the polymer.<br>7. Almost the entire organic polymer can be activated by the invented method. Minimum prerequisite of the polymer is that it should contain carbon-hydrogen bonds, which are available in almost all the polymers. |

The following examples describe the details of the invention, are produced by way of illustration only, and therefore should not be construed to limit the scope of the invention.

EXAMPLE 1

Optimization of Concentration Photolinker (FNAB) and its UV Exposure Time for Polystyrene Surface Activation Stock solution of the photolinker was made by dissolving 436.8 mg (2400 µM) of 1-fluoro-2-nitro-4-azidobenzene in 6 ml of methanol. From this stock solution 6.25 µl, 12.5 µl, 25 µl, 50 µl and 100 µl corresponding to 2.5 µM, 5 µM, 10 µM, 20 µM and 40 µM of the linker were poured into the corresponding triplicate wells of the polystyrene microtitre plate. The final volume of each well was made up to 100 µl by adding methanol. The plates were kept in the fume hood in dark or in dim light till the solvent was evaporated completely. Three more plates were prepared in the similar way. The plates were then irradiated by UV light at the wave length of 365 nm for 5, 10, 20, and 40 minutes respectively. The wells were washed thoroughly with methanol and allowed to air dry. To these activated plates 300 µl of (15 µg) HRP was added to each of its respective triplicate wells and the plates were incubated at 4° C. for 45 minutes. The wells were washed with washing buffer (PBS-tween 20) followed by the addition of substrate dye buffer (300 µl/well). The absorbance obtained at 490 nm showed the optimum concentration of the photolinker as well as the optimum irradiation time required for activation polystyrene surface (FIG. 1)

EXAMPLE 2

Optimization of HRP Concentration and its Incubation Time for Immobilization on the Activated Polystyrene Surface The wells of 96-well microtiter plate were loaded with FNAB (10 µM/50 µl $CH_3OH$ per well) and allowed to air dry in dark and then exposed to UV light at a wavelength of 365 nm for 20 minutes. The wells were washed thoroughly with methanol, air dried and kept at 4° C. in a sealed polyethylene bag until use. These activated plates were used for enzyme immobilization.

The stock solution of HRP was made in PBS (pH-7.2, 0.01M). Different concentrations of enzyme (0.937 µg/well-30 µg/well) were loaded on to the FNAB treated as well as untreated polystyrene wells and the final volume of each well was made up to 300 µl by adding buffer. The plates were incubated at 4° C. and 37° C. respectively for different time points (45 minutes & 4 flours) after which each well was washed thoroughly with washing buffer followed by the addition of substrate dye buffer (300 µl/well). The absorbance was recorded at 490 nm. (FIG. 2)

EXAMPLE 3

Comparative Study of Immobilized Enzyme on Two Different Plates

The wells of low binding microtiter plates and high binding Nunc maxisorp microtiter plates were activated as mentioned above using FNAB. Different amounts of HRP were used for immobilization on the activated and untreated wells. After washing the wells with washing buffer, HRP assay was carried out and the color produced was measured by ELISA reader at 490 nm (FIG. 3).

EXAMPLE 4

Optimization of the FNAB Concentration for Activation of Polystyrene Microtiter Wells by UV Light at 365 nm and Sunlight Different concentrations of FNAB (5-20 µmol/well/75 µl of methanol) were taken in different wells of a polystyrene microtiter plate, dried as described in example-1 and exposed to bright sunlight for 20 min. Simultaneously, activation experiments were carried out in U.V stratalinker by irradiating plates in U.V light for 20 minutes as in example-1.

After 20 min. both the plates were washed thoroughly with methanol. After immobilization of enzyme the plates were assayed as in example-1 (FIG. 4).

EXAMPLE 5

Optimization of the Time Required for Activation of Polystyrene Microtiter Wells by UV Light at 365 nm and Sunlight Three wells of each four plates were coated with photolinker (10 µmol/well/75 µl of methanol) irradiated for different period (5, 10, 20 and 30 min) by sunlight. Similar set of experiment is carried out in U.V stratalinker by irradiating plates in U.V light at 365 nm. The activation of the plates was evaluated by immobilizing and assaying the enzyme as described above ((FIG. 5).

EXAMPLE 6

Optimization of Amount of Photolinker and its UV Exposure Time for Activation of Wells of a Polypropylene Microtiter Plate FNAB solution was prepared by dissolving 436.8 mg (2400 µmol) of FNAB in 12 ml of methanol. From this solution, 12.5, 25, 50 and 100 µl aliquots, corresponding to 2.5, 5, 10 and 20 µmol, respectively of the linker, were poured into the corresponding triplicate wells of a PP microtiter plate. The final volume of each well was brought to 100 µl by adding methanol. The plate was kept in a fume hood in the dark, and methanol was evaporated slowly by gentle flow of air from a fan. Similarly, three more plates were coated with FNAB. The four coated plates were then exposed to UV light separately, for different time duration of 5, 10, 20, and 40 min, respectively in an UV stratalinker at the wavelength of 365 nm. After washing with methanol, 1.562 µg/well of horseradish peroxidase in 250 µl of phosphate-buffered saline (PBS, 0.01 M $Na_2HPO_4$. $2H_2O$, 0.01 M $NaH_2PO_4$, 0.85% NaCl, pH 7.2) was poured into each of the activated wells and the plates were incubated at 37° C. for 45 min. The wells were washed with washing buffer (0.1%Tween 20 in PBS) followed by addition of substrate-dye buffer (250 µl/well). The resultant solutions were transferred to the respective wells of a polystyrene microtiter plate and absorbance was recorded at 490 nm by an ELISA reader. The plates without FNAB treatment were used for control experiments (FIG. 6).

EXAMPLE 7

Stability of the Activated Plate

The wells of microtiter plates activated with FNAB were tightly sealed in polyethylene bags and kept at 37° C. and 4° C. for two months. After this period, 3.75 µg of HRP in 300 µl of buffer was added to the above activated as well as the freshly-activated wells (0 day-control) and allowed to immobilize for 45 min at 37° C. The wells were washed, substrate-dye buffer was added and absorbance was recorded at 490 nm.

Advantages

1. A simple, rapid and efficient method is invented for the preparation of an activated polymer surface.
2. Any polymer having a C—H bond can be activated by the invented method.
3. Using the invented method activation can be carried out under sunlight, which is abundant, freely available, non-hazardous and environmental friendly.
4. Activation of polymer can be carried out in a large scale by the invented method.
5. The invented activated surface can be used for immobilization of molecules, preferably biomolecules.
6. The invented activated surface can potentially be used in ELISA and other clinical diagnostics, molecular biology, proteomics, genomics, agriculture, environmental science, chemical or biochemical industry and many other related fields.

REFERENCES

1. Krysteva, M. A., Shopova, B. L., Yotova, I. Y., and Karasavova, M. I. (1991) Covalent binding of enzymes to synthetic membranes containing acrylamide units, using formaldehyde. Biotechnol Appl Biochem. 13, 106-111.
2. Pandey, P. C., Kayastha, A. M., and Pandey, V. (1992) Amperometric enzyme sensor for glucose based on graphite paste-modified electrodes. Appl. Biochem. Biotechnol. 33, 139-144.
3. Bangs, L. B., and Meza, M. B. (1995) Microspheres, part 2: Ligand attachment and test formulation. MD & DI's IVD Technol. 20-26.
4. Larsson, P. H., Johansson, S. G. O., Hult, A., and Gothe, S. (1987) Covalent binding of proteins to grafted plastic surfaces suitable for immunoassays. 1. Binding capacity and characteristics of grafted polymers. J Immunol Meth. 98, 129-135.
5. Rasmussen, S. R., Larsen, M. R., and Rasmussen, S. E. (1991) Covalent immobilization of DNA onto polystyrene microwells: The molecules are only bound at the 5' end. Anal Biochem. 198, 138-142.
6. Chevrier, D. Rasmussen, S. R., and Guesdon, J. L. (1993) PCR product quantification by nonradioactive hybridization procedures using an oligonucleotide covalently bound to microwells. Molec Cell Probes. 7, 187-197.
7. Amos, R. A. Anderson, A. B., and Clapper, D. L. (1995) Biomaterial surface modification using photochemical coupling technology. In Encyclopedic Handbook of Biomaterials and Bioengineering. Part A: New York, Marcel Dekker, 895-926.
8. Aleixo, J. A. G., Swaminathan, B., Minnich. S. A., Wallshein, V. A., 1985. Enzyme immunoassay: Binding of Salmonella antigens to activated microtiter plates. J. Immunoassay 6, 391.
9. de Queiroz, A. A., Barrak, E. R., Gil, H. A., and Higa, O. Z. (1997) Surface studies of albumin immobilized onto PE and PVC films. J. Biomater. Sci. Polym. 8, 667-681.
10. Kaetsu, I., Kumakura, M., Asano, M., Yamada, A., and Sakurai, Y. (1980) Immobilization of enzymes for medical uses on plastic surface by radiation-induced polymerization at low temperatures. J. Biomed. Mater. Res. 14, 199-210.
11. Sipehia, R., Chawla, A. S., Daka, J., and Chang, T. M. (1988) Immobilization of enzymes on polypropylene bead surfaces by anhydrous ammonia gaseous plasma technique. J Biomed. Mater. Res. 22, 417-422.
12. Sipehia, R. (1998-99) FTIR-ATR spectra of protein A immobilized onto functionalized polypropylene membranes by gaseous plasma of oxygen and of anhydrous ammonia. Biomater. Artif Cells Artif Organ 16, 955-966.
13. Hayat, U., Tinsley, A. M., Calder, M. R., and Clarke, D. J. (1992) ESCA investigation of low-temperature ammonia plasma-treated polyethylene substrate for immobilization of protein. Biomaterials 13, 801-806
14. Wang, C. C., and Hsiue, G. H. (1993) Immobilization of glucose oxidase on polyethylene film using a plasma induced graft copolymerization process. J. Biomater. Sci. Polym. 4, 357-367
15. Sano, S., Kato, K., and Ikada, Y. (1993) Introduction of functional groups onto the surface of polyethylene for protein immobilization. Biomaterials 14, 817-82
16. Terlingen, J. G., Brenneisen, L. M., Super, H. T., Pijpers, A. P., Hoffman, A. S., and Feijen, J. (1993) Introduction of amine groups on poly (ethylene) by plasma immobilization of a preadsorbed layer of decylamine hydrochloride. J. Biomater. Sci. Polym. 4, 165-181.
17. Nahar, P., Moza Wali, N., and Gandhi, R. P. (2001) Light-induced activation of an inert surface for covalent immobilization of a protein ligand. Anal. Biochem. 294, 148-153, doi: 10.1006/abio.2001.5168.
18. Patric, G. (1976) Photochemical immobilization of enzymes and other biochemicals. Method. Enzymol. 44, 280-288.
19. Ito, Y., Chen, G., and Imanishi, Y. (1996) Photoimmobilization of insulin onto polystyrene dishes for protein-free cell culture. Biotechnol.Prog. 12, 700-702.
20. Fleet, G. W. J., Knowles, J. R., and Porter, R. R. (1972) The antibody binding site. Labelling of a specific antibody against the photo-precursor of an aryl nitrene. Biochem. J. 128, 499-508.
21. Smith, P. K., Krohn, R. L., Hermanson, G. T., Mallia, A. K., Gartner, E. H., Provenzano, M. D., Fujimoto, E. K., Goeke, N. M., Olson, B. J., and Klenk, D. C. (1985) Measurement of protein using bicinchoninic acid. Analytical Biochemistry. 150, 76-85.
22. Dubucq, M., Hendrick, J. C., Osterrieth, P. M., Francois-C., and Franchimont, P. (1981) Enzymoimmunoassay of the main core protein (p28) of mouse mammary tumour virus (MMTV). Europ J Cancer. 17, 81-87.
23. Running, J. A., and Urdea, M. S. (1990) A procedure for productive coupling of synthetic oligonucleotides to polystyrene microtiter wells for hybridization capture. Bio-Techniques. 8, 276-277.

24. Guire, Enzyme immobilization with a thermochemical-photochemical bifunctional reagent, U.S. Pat. No. 3,959,078
25. Guire, Method of improving biocompatibility of solid surfaces, U.S. Pat. No. 4,973,493
26. Elsner, et al., Modification of polymer surfaces and molecular immobilization by photoreaction, U.S. Pat. No. 5,427,779
27. Jacobsen et al., Method of photochemical immobilization of ligands using quinones, PCT no. WO 96/31557
28. Jacobsen et al., Method of photochemical immobilization of ligands using quinones, U.S. Pat. No. 6,033,784

The invention claimed is:

1. A photochemical process using unmodified 1-fluoro-2-nitro-4-azidobenzene for the preparation of an activated polymer surface having an active fluoro group and immobilization of a biomolecule thereon via a covalent bond between the activated polymer surface and the biomolecule, the process comprising the steps of:
    (a) pouring a solution of unmodified 1-fluoro-2-nitro-4-azidobenzene in an organic solvent onto a polymer surface so as to coat the polymer surface,
    (b) evaporating the organic solvent at room temperature in the dark so as to thereby form a 1-fluoro-2-nitro-4-azidobenzene coated polymer surface,
    (c) subjecting the 1-fluoro-2-nitro-4-azidobenzene coated polymer surface of step (b) to photoirradiation for a period ranging from 1 second to 60 minutes,
    (d) washing the irradiated, coated polymer surface from step (c) with an organic solvent,
    (e) evaporating any organic solvent remaining after washing the polymer surface from step (d) at ambient temperature to obtain an activated polymer surface having an active fluoro group,
    (f) placing the biomolecule in contact with the activated polymer surface from step (e), and
    (g) incubating the activated polymer surface in contact with the biomolecule from step (f) so as to displace the active fluoro group and thereby form the covalent bond between the activated polymer surface and the biomolecule and thereby immobilize the biomolecule on the polymer surface.

2. The process as claimed in claim 1, wherein in the step (a) the polymer surface is selected from the group consisting of polystyrene, polyethylene, polypropylene, polycarbonate, polyvinyl alcohol and polyvinyl chloride.

3. The process as claimed in claim 1, wherein in step (a) the polymer surface is selected from the group consisting of surfaces in the shape of a stick, a microtiter plate, a sheet, a tube, a well, and a cuvet.

4. The process as claimed in claim 1, wherein in step (c) the source of photoirradiation is selected from the group consisting of UV light, sunlight, flash light, and laser beam.

5. The process as claimed in claim 1, wherein the biomolecule is selected from the group consisting of an enzyme, an antigen, an antibody, and a peptide.

6. The process as claimed in claim 1, wherein the activated surface is capable of forming a covalent bond with the biomolecule within 30 minutes to 5 hours.

7. The process as claimed in claim 1, wherein in step (a) the organic solvent is capable of dissolving the 1-fluoro-2-nitro-4-azidobenzene but not the polymer.

8. A photochemical process using unmodified 1-fluoro-2-nitro-4-azidobenzene for the preparation of an activated polymer surface having an active fluoro group and immobilization of a biomolecule containing an amino group thereon via a covalent bond between the activated polymer surface and the biomolecule, the process comprising the steps of;
    (a) coating the surface of a polymer having a carbon-hydrogen bond with unmodified 1-fluoro-2-nitro-4-azidobenzene in an organic solvent,
    (b) evaporating the organic solvent at room temperature in the dark so as to thereby form a 1-fluoro-2-nitro-4-azidobenzene coated polymer surface,
    (c) subjecting the 1-fluoro-2-nitro-4-azidobenzene coated polymer surface of step (b) to photoirradiation for a period ranging from 1 second to 60 minutes,
    (d) washing the irradiated, coated polymer surface from step (c) with an organic solvent,
    (e) evaporating any organic solvent remaining after washing the polymer surface from step (d) at ambient temperature to obtain an activated polymer surface having an active fluoro group,
    (f) placing the biomolecule in contact with the activated polymer surface from step (e), and
    (g) incubating the activated polymer surface in contact with the biomolecule from step (f) so as to displace the active fluoro group and thereby form the covalent bond between the activated polymer surface and the amino group of the biomolecule and thereby immobilize the biomolecule on the polymer surface.

* * * * *